United States Patent [19]

Frankel et al.

[11] 4,147,731
[45] Apr. 3, 1979

[54] PROCESS FOR NITROFORM ISOLATION

[75] Inventors: Milton B. Frankel, Tarzana; Frederick D. Raniere, Northridge; Wallace W. Thompson, Tarzana; Edward F. Witucki, Van Nuys; Dean O. Woolery, II, Reseda, all of Calif.

[73] Assignee: Rockwell International Corporation, El Segundo, Calif.

[21] Appl. No.: 871,904

[22] Filed: Jan. 24, 1978

[51] Int. Cl.$^2$ .............................................. C07C 76/02
[52] U.S. Cl. .................................................. 260/644
[58] Field of Search ........................................ 260/644

[56] References Cited

PUBLICATIONS

Urbanski, Chemistry and Technology of Explosives, vol. 1, The MacMillan Company, New York, 1964, pp. 587 and 588.

Primary Examiner—Leland A. Sebastian
Attorney, Agent, or Firm—L. Lee Humphries; Robert M. Sperry

[57] ABSTRACT

A method of isolating nitroform from a solution of nitric acid, nitroform, and water by adding sulfuric acid and preferentially extracting the nitroform with methylene chloride. The nitroform is then extracted from the methylene chloride solution into water. It is a particular advantage of the present method that no distillations involving nitroform are required.

5 Claims, No Drawings

PROCESS FOR NITROFORM ISOLATION

The invention herein described was made in the course of or under contract or subcontract thereunder (or grant) with the United States Air Force.

BACKGROUND OF THE INVENTION

1. Field of the Invention

The present invention concerns an improved method for the isolation of trinitromethyl compounds. Specifically, the present invention relates to a method for the isolation of trinitromethane (nitroform) by the addition of sulfuric acid to a nitration mixture of nitric acid, nitroform, and water, and perferentially extracting the nitroform with an organic solvent such as methylene chloride. The nitroform is then extracted from the methylene chloride into water.

Nitroform (trinitromethane) is a very valuable compound for use in the preparation of explosive and propellant ingredients, due to its high oxygen content and labile hydrogen atom, which facilitates the preparation of trinitromethyl and fluorodinitromethyl derivatives. Of particular interest, is the use of nitroform for the preparation of bis(fluorodinitroethyl) formal (FEFO) and 1,3-bis(fluorodinitroethoxy)-2,2-bis(difluoroamino) propane (SYEP). Both FEFO and SYEP are energetic plasticizers that are being utilized in advanced solid propellants. Consequently, low-cost processes for their production are required. This, of course, necessitates starting their production with low-cost nitroform.

2. Description of the Prior Art

An industrial scale facility for the production of trinitromethane based on the reaction between acetylene and nitric acid has been developed by Nitro Nobel, as shown in the article by Wetterhold, in G. A., *Tetrahedron*, 19, Suppl. 1, 155 (1963). The product from this nitration consists of a mixture with the nominal composition of approximately 76% HNO$_3$/13% Nitroform/10% H$_2$O. A method for the recovery of nitroform from this mixture was developed by Nitro Nobel as shown in U.S. Pat. Nos. 2,658,084 and 3,880,941.

In this procedure, the strong nitric acid is first distilled from the reaction mixture. Water is then added to the distillation bottoms and the nitroform-water azeotrope is then distilled off. This procedure, thus, involves two distillations in which nitroform is involved. Since nitroform is an energetic explosive compound with limited thermal stability, the distillation of even nitroform solutions represents a potentially hazardous operation.

SUMMARY OF THE INVENTION

A solvent extraction method has now been developed for the isolation of nitroform from the nitroform, nitric acid, water mixture, which involves no distillations containing nitroform. The inherent safety advantages of this new process are obvious. The new process for the isolation of nitroform involves adding concentrated sulfuric acid to the mixture obtained from the nitration of acetylene, which has the nominal composition of 76 HNO$_3$/13 NF/10 H$_2$O, extracting preferentially the nitroform from this mixture with methylene chloride, and then extracting the nitroform from the methylene chloride solution into water. The safety and simplicity of this new process is readily apparent when one compares it with the old distillation process (Table I).

An added feature of this new extraction process is that the aqueous nitroform solution contains very little nitric acid. This is important in the preparation of fluorotrinitromethane, the intermediate to FEFO, which is prepared by the fluorination of the aqueous nitroform. The very explosive fluorine nitrate gas is readily formed by the action of fluorine on nitric acid; this would be highly undesirable in a production process. A sample of the aqueous nitroform, isolated by the extraction process, was fluorinated to fluorotrinitromethane, and no fluorine nitrate was detected in the gas stream.

DESCRIPTION OF THE PREFERRED EMBODIMENTS

The method of the present invention is applicable to both batch and continuous methods for the isolation of nitroform. It will be obvious to those skilled in the art that other concentrations of sulfuric acid could be used to retain the nitric acid during the extraction process. The 96–98% sulfuric acid is preferred in view of its cost, availability, and effectiveness in retaining nitric acid.

It will also be obvious to those skilled in the art that other organic solvents would be useful in extracting the nitroform from the acid mixture. Methylene chloride is preferred in view of its cost, availability, and its efficiency in extracting nitroform from the acid mixture.

The reaction temperature is not particularly critical. The extractions could be carried out over a temperature range of 10°–25° C. The preferred temperature is ambient since it is the most convenient for carrying out in practice. Pressure has not been found to be a particularly critical parameter in accordance with the present method. Accordingly, the method of the present invention advantageously is practiced at about ambient pressure.

The following examples are set forth to further illustrate the method of the present invention. The nitroform utilized in this work was prepared by the nitration of isopropyl alchohol, as disclosed in copending patent application Ser. No. 857,055 filed Dec. 5, 1977.

TABLE 1

ISOLATION OF NITROFORM

Distillation Process

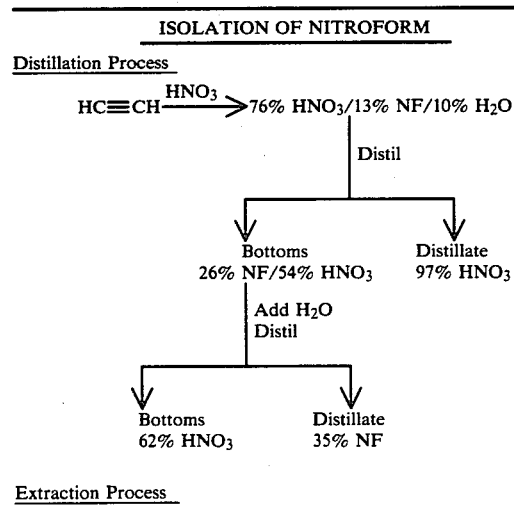

Extraction Process

TABLE 1-continued
ISOLATION OF NITROFORM

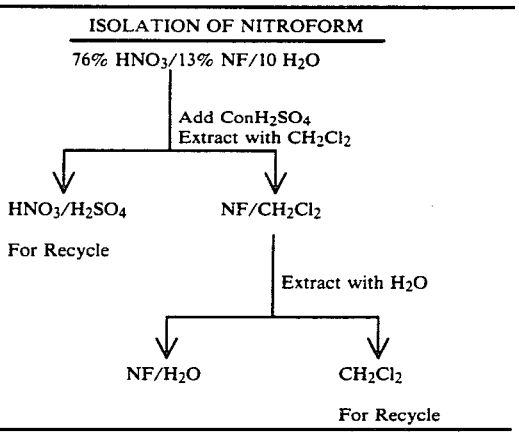

EXAMPLE I

The nitration mixture of 198 g, consisting of approximately 76% $HNO_3$/13%NF/10%$H_2O$ was cooled to 5°–10° C. and 346 g of concentration sulfuric acid was added. The acid mixture was extracted with 3×100 ml of methylene chloride. Extraction of the methylene chloride solution with water gave 20.3 g (78% recovery) of nitroform.

EXAMPLE II

The following example is set forth to demonstrate the method of the present invention as applied to a continuous process for the isolation of nitroform.

Two countercurrent liquid extractors were set up in conjunction with each other. The extractors consisted of glass column (30"×1"), packed with glass Raschig rings, with inlets at the bottom and top of each column. In the first column, methylene chloride was fed continuously into the bottom of the column while the acid nitration mixture of $HNO_3$/NF/$H_2O$/$H_2SO_4$ was added simultaneously at the top of the column. The heavier acid layer passed to the bottom of the column and then could be recycled. The methylene chloride extracted the nitroform from the acid solution and came out of the top of the first column and was passed into the top of the second column. Water was simultaneously being introduced through the bottom of the second column. The water extracted the nitroform from the methylene chloride and the aqueous nitroform solution came out the top of the second column while the methylene chloride solution excited at the bottom. The aqueous nitroform solution and the methylene chloride solution were then recycled.

In a typical run, an acid mixture of 300 g 90% nitric acid, 408 g sulfuric acid, and 103 g nitroform was introduced at the top of the first column while 2000 ml of methylene chloride was introduced at the bottom of the column. The methylene chloride solution of nitroform passed into the top of the second column while 2000 ml of water was introduced at the bottom of the second column. After one cycle, analysis of the effluent solutions for nitroform showed 8.9% in the aqueous stream. The remaining 50% of the nitroform was retained in the solutions remaining in the columns. By a continuous recycle of the solutions, the remaining nitroform was extracted into the aqueous solution.

EXAMPLE III
Fluorination of Aqueous Nitroform

A solution of 17.5 g (0.11 mole) of nitroform, from Example I, and 60 ml of water was cooled in an ice bath and a mixture of fluorine and nitrogen was passed through the solution for 90 minutes. Analysis (G.C.) of the gas stream showed no $FNO_3$, confirming that there was no nitric acid in the aqueous nitroform. The fluorotrinitromethane separated as an insoluble layer. The yield was 12.4 g (63.4%) with a G.C. purity of 99%.

Obviously, numerous variations and modifications can be made without departing from the present invention. Accordingly, it should be clearly understood that the forms of the present invention described above are illustrative only and are not intended to limit the scope of the present invention.

We claim:
1. A method of isolating nitroform, comprising the steps of:
   adding sulfuric acid to the nitration mixture of nitric acid/nitroform/water,
   preferentially extracting the nitroform from the acid solution using an organic solvent, and
   extracting the nitroform from the organic solvent solution in water.
2. The method of claim 1 wherein the sulfuric acid is about 96–98% pure.
3. The method of claim 1 wherein the organic solvent is methylene chloride.
4. The method of claim 1 wherein the extraction is carried out in a temperature range of 10°–25° C. and at ambient pressure.
5. A method of isolating nitroform by continuously extracting preferentially nitroform from a solution of nitric acid, nitroform, and water with methylene chloride and then extracting continuously the nitroform from the methylene chloride solution into water.

* * * * *